(12) United States Patent
Everett et al.

(10) Patent No.: US 10,004,428 B2
(45) Date of Patent: Jun. 26, 2018

(54) PERIPHERAL SENSORY AND SUPERSENSORY REPLACEMENT SYSTEM

(75) Inventors: Breanne Everett, Calgary (CA); Marcel Groenland, Calgary (CA)

(73) Assignee: Orpyx Medical Technologies, Inc., Calgary (CA)

( * ) Notice: Subject to any disclaimer, the term of this patent is extended or adjusted under 35 U.S.C. 154(b) by 0 days. days.

(21) Appl. No.: 13/284,592

(22) Filed: Oct. 28, 2011

(65) Prior Publication Data
US 2012/0109013 A1    May 3, 2012

Related U.S. Application Data

(60) Provisional application No. 61/408,373, filed on Oct. 29, 2010.

(51) Int. Cl.
*A61B 5/103* (2006.01)
*A61B 5/00* (2006.01)

(52) U.S. Cl.
CPC .......... *A61B 5/1036* (2013.01); *A61B 5/1038* (2013.01); *A61B 5/4047* (2013.01); *A61B 5/6807* (2013.01); *A61B 5/72* (2013.01); *A61B 5/7455* (2013.01); *A61B 2562/046* (2013.01)

(58) Field of Classification Search
USPC .......... 600/587, 549, 504, 481, 407; 604/66
See application file for complete search history.

(56) References Cited

U.S. PATENT DOCUMENTS 3,791,375 A   2/1974  Pfeiffer
4,251,302 A   2/1981  Leonard et al.
4,554,930 A   11/1985 Kress
4,647,918 A   3/1987  Goforth
5,010,772 A   4/1991  Bourland et al.
5,033,291 A   7/1991  Podoloff et al.
5,054,323 A   10/1991 Hubbard, Jr. et al.
5,505,072 A   4/1996  Oreper et al.
5,642,096 A   6/1997  Leyerer et al.
(Continued)

FOREIGN PATENT DOCUMENTS

CA   2306967 A1   4/1999
CA   2352768 A1   6/1999
(Continued)

OTHER PUBLICATIONS

Extended European Search Report dated Mar. 3, 2014 in Patent Application No. 11835396.0.
(Continued)

*Primary Examiner* — Matthew Kremer
(74) *Attorney, Agent, or Firm* — Oblon, McClelland, Maier & Neustadt, L.L.P.

(57) ABSTRACT

A sensor-based quantification and analysis system includes an input device including a plurality of sensors that generate an input based on a force. The input device also includes a transmission device that transmits force information based on the input. The system also includes an output device that receives the force information. A processing unit selects, for each of the plurality of sensors, one of a plurality of levels of a likelihood of tissue damage based on the force and a predetermined time period. Further, the output device includes a display that presents or logs the one of the plurality of levels of the likelihood of tissue damage for each of the plurality of sensors.

19 Claims, 8 Drawing Sheets

(56) References Cited

U.S. PATENT DOCUMENTS

| | | |
|---|---|---|
| 5,678,448 A | 10/1997 | Fullen et al. |
| 5,678,566 A | 10/1997 | Dribbon |
| 5,689,455 A | 11/1997 | Mullarkey et al. |
| 5,756,904 A | 5/1998 | Oreper et al. |
| 5,879,292 A | 3/1999 | Sternberg et al. |
| 5,905,209 A | 5/1999 | Oreper |
| 6,025,725 A | 2/2000 | Gershenfeld et al. |
| 6,030,351 A | 2/2000 | Schmidt et al. |
| 6,055,173 A | 4/2000 | Mullarkey et al. |
| 6,130,834 A | 10/2000 | Mullarkey et al. |
| 6,155,120 A | 12/2000 | Taylor |
| 6,272,936 B1 | 8/2001 | Oreper et al. |
| 6,273,863 B1 | 8/2001 | Avni et al. |
| 6,287,253 B1 | 9/2001 | Ortega et al. |
| 6,360,597 B1 | 3/2002 | Hubbard, Jr. |
| 6,445,605 B1 | 9/2002 | Mullarkey et al. |
| 6,661,693 B2 | 12/2003 | Mullarkey et al. |
| 6,694,826 B2 | 2/2004 | Kiribayashi et al. |
| 6,712,084 B2 | 3/2004 | Shajii et al. |
| 6,807,869 B2 | 10/2004 | Farringdon et al. |
| 6,810,308 B2 | 10/2004 | Shajii et al. |
| 6,826,071 B2 | 11/2004 | Mullarkey et al. |
| 6,829,942 B2 | 12/2004 | Yanai et al. |
| 6,868,862 B2 | 3/2005 | Shajii et al. |
| 6,903,991 B2 | 6/2005 | Mullarkey et al. |
| 6,932,098 B2 | 8/2005 | Shajii et al. |
| 6,948,508 B2 | 9/2005 | Shajii et al. |
| 6,963,772 B2 | 11/2005 | Bloom et al. |
| 7,004,191 B2 | 2/2006 | Shajii et al. |
| 7,030,764 B2 | 4/2006 | Smith et al. |
| 7,136,767 B2 | 11/2006 | Shajii et al. |
| 7,260,999 B2 | 8/2007 | Divigalpitiya et al. |
| 7,424,346 B2 | 9/2008 | Shajii et al. |
| 7,535,108 B2 | 5/2009 | Saimen |
| 7,552,015 B2 | 6/2009 | Shajii et al. |
| 7,587,937 B2 | 9/2009 | Haselhurst et al. |
| 7,597,676 B2 | 10/2009 | Dunn et al. |
| 7,625,117 B2 | 12/2009 | Haslett et al. |
| 7,632,239 B2 | 12/2009 | Dar et al. |
| 7,687,678 B2 | 3/2010 | Jacobs |
| 7,716,005 B2 | 5/2010 | Shoureshi et al. |
| 7,726,206 B2 | 6/2010 | Terrafranca, Jr. et al. |
| 7,809,473 B2 | 10/2010 | Shajii et al. |
| 7,869,164 B2 | 1/2011 | Shin |
| 8,011,041 B2 | 9/2011 | Hann |
| 8,111,165 B2 | 2/2012 | Ortega et al. |
| 8,121,800 B2 | 2/2012 | Altman et al. |
| 8,150,553 B2 | 4/2012 | Shajii et al. |
| 8,285,356 B2 | 10/2012 | Bly et al. |
| 8,308,714 B2 | 11/2012 | Weston et al. |
| 8,454,539 B2 | 6/2013 | Vuillerme et al. |
| 8,535,246 B2 | 9/2013 | Drennan et al. |
| 8,738,187 B2 | 5/2014 | Shajii et al. |
| 8,994,528 B2 | 3/2015 | Celik-Butler et al. |
| 9,188,963 B2 | 11/2015 | Gray et al. |
| 9,204,797 B2 | 12/2015 | Gray et al. |
| 9,451,881 B2 | 9/2016 | Gray et al. |
| 2001/0044588 A1* | 11/2001 | Mault ............... 600/549 |
| 2002/0163827 A1 | 11/2002 | Mullarkey et al. |
| 2002/0167831 A1 | 11/2002 | Mullarkey et al. |
| 2003/0185080 A1 | 10/2003 | Mullarkey et al. |
| 2003/0234039 A1 | 12/2003 | Shajii et al. |
| 2003/0234044 A1 | 12/2003 | Shajii et al. |
| 2003/0234045 A1 | 12/2003 | Shajii et al. |
| 2003/0234046 A1 | 12/2003 | Shajii et al. |
| 2003/0234047 A1 | 12/2003 | Shajii et al. |
| 2003/0234048 A1 | 12/2003 | Shajii et al. |
| 2003/0236592 A1 | 12/2003 | Shajii et al. |
| 2003/0236638 A1 | 12/2003 | Shajii et al. |
| 2003/0236643 A1 | 12/2003 | Shajii et al. |
| 2004/0019259 A1* | 1/2004 | Brown et al. ............... 600/300 |
| 2004/0133120 A1* | 7/2004 | Frei et al. .................. 600/544 |
| 2004/0223397 A9 | 11/2004 | Mullarkey et al. |
| 2004/0256003 A1 | 12/2004 | Shajii et al. |
| 2005/0004500 A1 | 1/2005 | Rosser et al. |
| 2005/0066407 A1 | 3/2005 | Delaney |
| 2005/0096513 A1 | 5/2005 | Ozguz et al. |
| 2005/0131317 A1 | 6/2005 | Oddsson et al. |
| 2005/0148904 A1 | 7/2005 | Mimura et al. |
| 2005/0165284 A1* | 7/2005 | Gefen ............... 600/300 |
| 2005/0190531 A1 | 9/2005 | Gall et al. |
| 2005/0197540 A1 | 9/2005 | Liedtke |
| 2005/0201135 A1 | 9/2005 | Mullarkey et al. |
| 2006/0016255 A1 | 1/2006 | Haselhurst et al. |
| 2006/0282017 A1 | 2/2006 | Avni et al. |
| 2006/0052678 A1 | 3/2006 | Drinan et al. |
| 2006/0110049 A1* | 5/2006 | Liang et al. ............... 382/224 |
| 2006/0173642 A1 | 8/2006 | Shajii et al. |
| 2007/0038042 A1* | 2/2007 | Freeman et al. ............... 600/310 |
| 2007/0173903 A1 | 7/2007 | Goren et al. |
| 2007/0203533 A1 | 8/2007 | Goren et al. |
| 2007/0227762 A1 | 10/2007 | Yang et al. |
| 2007/0234825 A1 | 10/2007 | Loomis et al. |
| 2007/0250286 A1 | 10/2007 | Duncan et al. |
| 2007/0282562 A1 | 12/2007 | Schwartz et al. |
| 2008/0091306 A1 | 4/2008 | Shajii et al. |
| 2008/0098820 A1 | 5/2008 | Morsch et al. |
| 2008/0167580 A1 | 7/2008 | Avni et al. |
| 2008/0171957 A1 | 7/2008 | Connolly et al. |
| 2008/0287832 A1 | 11/2008 | Collins et al. |
| 2008/0306352 A1* | 12/2008 | Beiswenger et al. ............... 600/301 |
| 2008/0306407 A1 | 12/2008 | Taylor |
| 2008/0307899 A1 | 12/2008 | Von Lilienfeld-Toal et al. |
| 2009/0036885 A1* | 2/2009 | Gregg ............... 606/35 |
| 2009/0048070 A1* | 2/2009 | Vincent et al. ............... 482/8 |
| 2009/0069865 A1 | 3/2009 | Lasko et al. |
| 2009/0070939 A1* | 3/2009 | Hann ............... 5/652.1 |
| 2009/0099471 A1* | 4/2009 | Broadley et al. ............... 600/532 |
| 2009/0156988 A1 | 6/2009 | Ferren et al. |
| 2009/0157054 A1 | 6/2009 | Ferren et al. |
| 2009/0157055 A1 | 6/2009 | Ferren et al. |
| 2009/0157056 A1 | 6/2009 | Ferren et al. |
| 2009/0157057 A1 | 6/2009 | Ferren et al. |
| 2009/0157058 A1 | 6/2009 | Ferren et al. |
| 2009/0157171 A1 | 6/2009 | Ferren et al. |
| 2009/0163856 A1 | 6/2009 | Ferren et al. |
| 2009/0209830 A1 | 8/2009 | Nagle et al. |
| 2009/0234249 A1 | 9/2009 | Randolph |
| 2009/0267783 A1 | 10/2009 | Vock et al. |
| 2009/0281412 A1 | 11/2009 | Boyden et al. |
| 2009/0281413 A1 | 11/2009 | Boyden et al. |
| 2009/0284378 A1 | 11/2009 | Ferren et al. |
| 2009/0287093 A1 | 11/2009 | Ferren et al. |
| 2009/0287094 A1 | 11/2009 | Ferren et al. |
| 2009/0287101 A1 | 11/2009 | Ferren et al. |
| 2009/0287109 A1 | 11/2009 | Ferren et al. |
| 2009/0287110 A1 | 11/2009 | Ferren et al. |
| 2009/0287120 A1 | 11/2009 | Ferren et al. |
| 2009/0287191 A1 | 11/2009 | Ferren et al. |
| 2009/0292195 A1 | 11/2009 | Boyden et al. |
| 2009/0292212 A1 | 11/2009 | Ferren et al. |
| 2009/0292213 A1 | 11/2009 | Ferren et al. |
| 2009/0292214 A1 | 11/2009 | Ferren et al. |
| 2009/0292222 A1 | 11/2009 | Ferren et al. |
| 2009/0293319 A1 | 12/2009 | Avni |
| 2009/0318802 A1 | 12/2009 | Boyden et al. |
| 2010/0004566 A1 | 1/2010 | Son et al. |
| 2010/0036209 A1 | 2/2010 | Ferren et al. |
| 2010/0036263 A1 | 2/2010 | Ferren et al. |
| 2010/0036268 A1 | 2/2010 | Ferren et al. |
| 2010/0036269 A1 | 2/2010 | Ferren et al. |
| 2010/0081890 A1* | 4/2010 | Li et al. ............... 600/301 |
| 2010/0107770 A1 | 5/2010 | Serban et al. |
| 2010/0201650 A1 | 8/2010 | Son |
| 2010/0210975 A1* | 8/2010 | Anthony, III ........ A61B 5/0002 600/595 |
| 2010/0210983 A1 | 8/2010 | Baker et al. |
| 2010/0210988 A1 | 8/2010 | Dallison et al. |
| 2010/0249553 A1 | 9/2010 | Maclaughlin |
| 2010/0292600 A1* | 11/2010 | Dibenedetto ...... A63B 24/0062 600/520 |
| 2010/0324743 A1 | 12/2010 | Shajii et al. |
| 2011/0015498 A1 | 1/2011 | Mestrovic et al. |

(56) References Cited

U.S. PATENT DOCUMENTS

| | | | |
|---|---|---|---|
| 2011/0054270 A1* | 3/2011 | Derchak | A61B 5/0002 600/300 |
| 2011/0054359 A1* | 3/2011 | Sazonov et al. | 600/595 |
| 2011/0054809 A1* | 3/2011 | Templeman | A61B 5/1118 702/44 |
| 2011/0087445 A1* | 4/2011 | Sobolewski | 702/44 |
| 2011/0178375 A1 | 7/2011 | Forster | |
| 2011/0184257 A1 | 7/2011 | Boll et al. | |
| 2011/0230732 A1 | 9/2011 | Edman et al. | |
| 2011/0263950 A1 | 10/2011 | Larson et al. | |
| 2011/0319787 A1 | 12/2011 | Lamoise et al. | |
| 2012/0004566 A1* | 1/2012 | Zhang | A61B 5/0464 600/515 |
| 2012/0174992 A1 | 7/2012 | Shajii et al. | |
| 2012/0245439 A1 | 9/2012 | Andre et al. | |
| 2013/0041235 A1 | 2/2013 | Rogers et al. | |
| 2013/0066168 A1 | 3/2013 | Yang et al. | |
| 2013/0102930 A1 | 4/2013 | Connor | |
| 2013/0120157 A1 | 5/2013 | Geva | |
| 2013/0137943 A1 | 5/2013 | Pinto | |
| 2013/0271278 A1 | 10/2013 | Duesterhoft et al. | |
| 2014/0005618 A1 | 1/2014 | Locke et al. | |
| 2014/0150571 A1 | 6/2014 | Kuniyoshi et al. | |

FOREIGN PATENT DOCUMENTS

| | | | |
|---|---|---|---|
| CA | 2376162 A1 | 1/2001 | |
| CA | 2411394 A1 | 12/2001 | |
| CA | 2528218 A1 | 12/2004 | |
| CA | 2604633 A1 | 10/2005 | |
| CA | 2538940 A1 | 6/2006 | |
| CA | 2590870 A1 | 7/2006 | |
| CA | 2583034 A1 | 9/2007 | |
| CA | 2654388 A1 | 1/2008 | |
| CA | 2656733 A1 | 1/2008 | |
| CA | 2696932 A1 | 2/2009 | |
| CA | 2701238 A1 | 4/2009 | |
| CA | 2744215 A1 | 6/2010 | |
| CA | 2753063 A1 | 10/2010 | |
| CA | 2767292 A1 | 1/2011 | |
| CA | 2786524 A1 | 7/2011 | |
| CA | 2815963 A1 | 5/2012 | |
| CN | 103025230 A | 4/2013 | |
| EP | 1207785 A1 | 5/2002 | |
| EP | 1 488 744 A1 | 12/2004 | |
| EP | 0 835 045 B1 | 6/2006 | |
| EP | 1 785 706 A1 | 5/2007 | |
| EP | 2143090 A1 | 1/2010 | |
| GB | 2 445 760 A | 7/2008 | |
| JP | 8-238275 A | 9/1996 | |
| WO | WO 01/00089 A1 | 1/2001 | |
| WO | WO 01/36051 A2 | 5/2001 | |
| WO | 03/079898 A1 | 10/2003 | |
| WO | WO 03/086235 A2 | 10/2003 | |
| WO | WO 2007/106040 A1 | 9/2007 | |
| WO | WO2008/088985 * | 7/2008 | A61N 1/04 |
| WO | WO 2009/005373 A1 | 1/2009 | |
| WO | WO 2009/132465 A1 | 11/2009 | |
| WO | WO 2010/096691 A2 | 8/2010 | |
| WO | WO 2010/119441 A2 | 10/2010 | |
| WO | WO 2011/091517 A1 | 8/2011 | |

OTHER PUBLICATIONS

Notice of Acceptance dated Jul. 1, 2015 in New Zealand Patent Application No. 611197.
Australian Examination Report dated May 13, 2015 in Patent Application No. 2011320072.
Office Action dated Jun. 30, 2015 in Japanese Patent Application No. 2013-535218 (with English language translation).
Darrell Etherington, "Apple Patents Smart Shoes That Feature Embedded Sensors, and Alarms for When You Need New Ones" TechCrunch Survey, http://techcrunch.com/2013/01/24/apple-patents-smart-shoes-that-feature-embedded-sensors-and-alarms-for-when-you-need-new-ones/ , Posted Jan. 24, 2013, 8 Pages. (corresponds to US 2009/0267783 A1).
"Electronic sensor technologies for wounds", Delta, Path-monitoring, Rev. Sep. 26, 2012, pp. 4-23 with cover pages.
"Smart bandage", The Engineer, vol. 10, Apr. 6, 2009, 2 Pages.
Augustin Grillet, et al., "Optical fiber sensors embedded into medical textiles for healthcare monitoring", IEEE Sensors Journal, vol. 8, No. 7, Jul. 2008, pp. 1215-1222.
International Search Report and Written Opinion dated Aug. 19, 2014 in corresponding PCT/CA2014/050471.
Office Action dated Feb. 16, 2016 in Japanese Patent Application No. 2013-535218 (English translation only).
Notice of Acceptance dated May 5, 2016, in Australian Patent Application No. 2011320072.
Notice of Allowance dated Aug. 2, 2016, in Japanese Patent Application No. 2013-535218 (with English-language translation).
Extended European Report dated Jan. 19, 2017 in Patent Application No. 14801355.0.
Office Action dated Dec. 19, 2016 in co-pending U.S. Appl. No. 14/283,921.
International Preliminary Report on Patentability issued in PCT/CA2011/001200 dated May 10, 2013.
International Preliminary Report on Patentability issued in PCT/CA2014/050471 dated Dec. 3, 2015.
US Notice of Allowance issued in U.S. Appl. No. 14/283,921 dated Apr. 5, 2017.
Canadian Office Action issued in Application No. 2,813,656 dated May 12, 2017.
Gafurov et al., "Biometric Gait Authentication Using Accelerometer Sensor," Journal of Computers, Nov. 2006, vol. 1 (7), pp. 51-59.
Huang et al., "Gait Modeling for Human Identification," Robotics and Automation, IEEE International Conference on, Apr. 10-14, 2007, pp. 4833-4838.
Kong et al., "A Gait Monitoring System Based on Air Pressure Sensors Embedded in a Shoe," IEEE/ASME Transactions on Mechatronics, Jun. 2009, vol. 14 (3), pp. 358-370.
Yamakawa et al., "Biometric Personal Identification Based on Gait Pattern Using Both Feet Pressure Change," World Automation Congress, Sep. 2008, pp. 1-6.
International Search Report dated Feb. 1, 2012 in PCT/CA2011/001200 with Written Opinion.
European Office Action dated Sep. 15. 2017 for European Patent Application No. 11835396.0, Communication pursuant to Article 94(3) EPC, in English.
Chinese Office Action issued in Application No. CN201480041466.4 dated Dec. 22, 2017 (w/ English Translation), citing documents AA and AO therein.

* cited by examiner

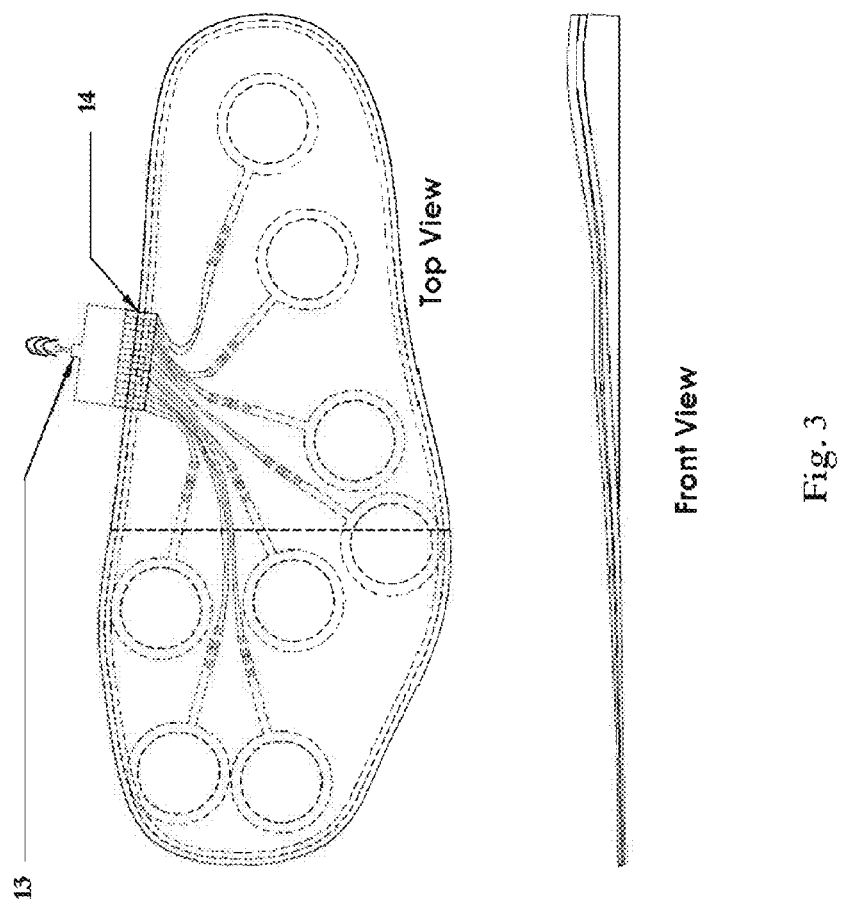
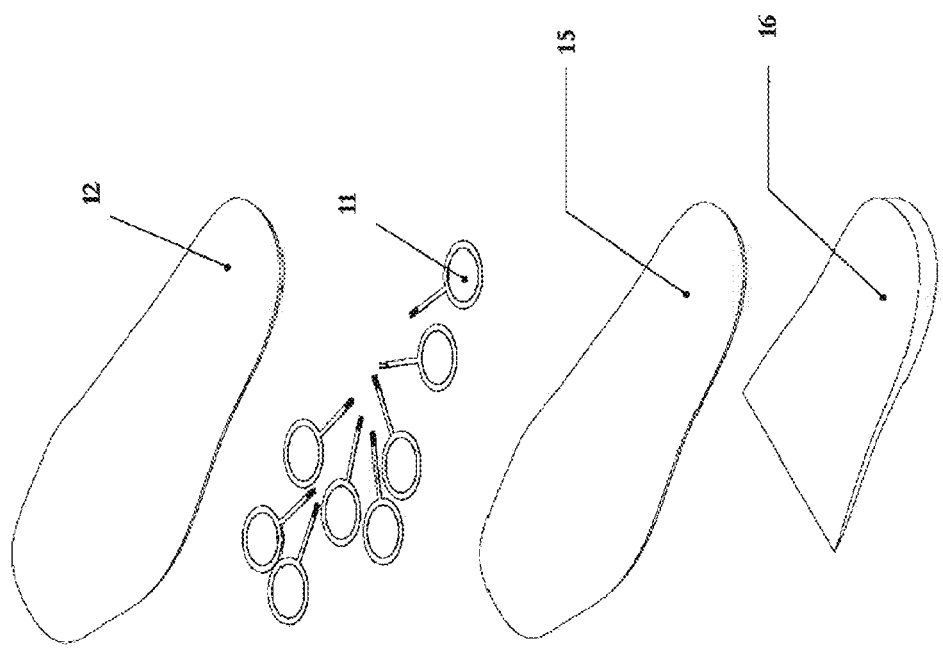
Fig. 3

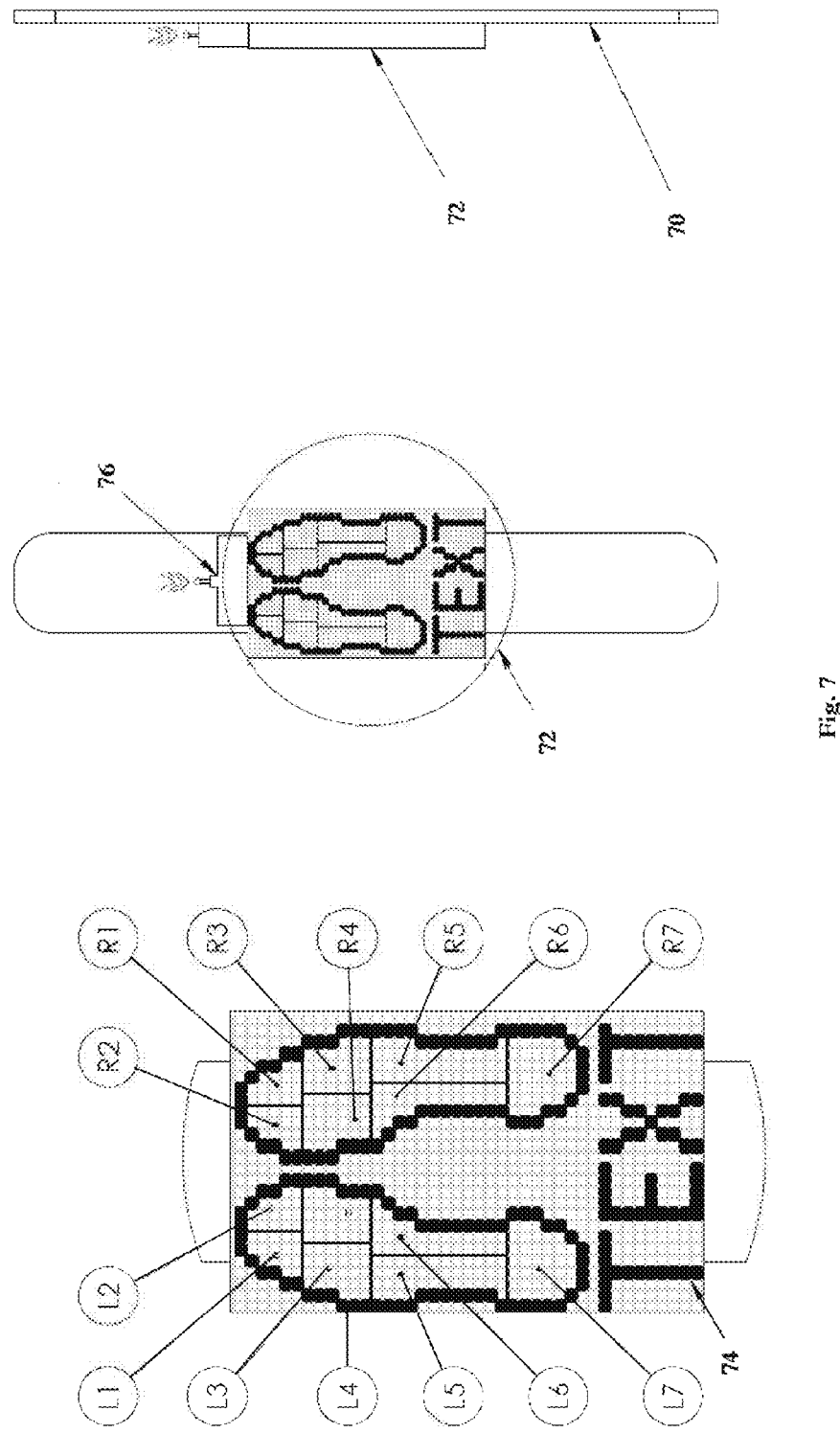

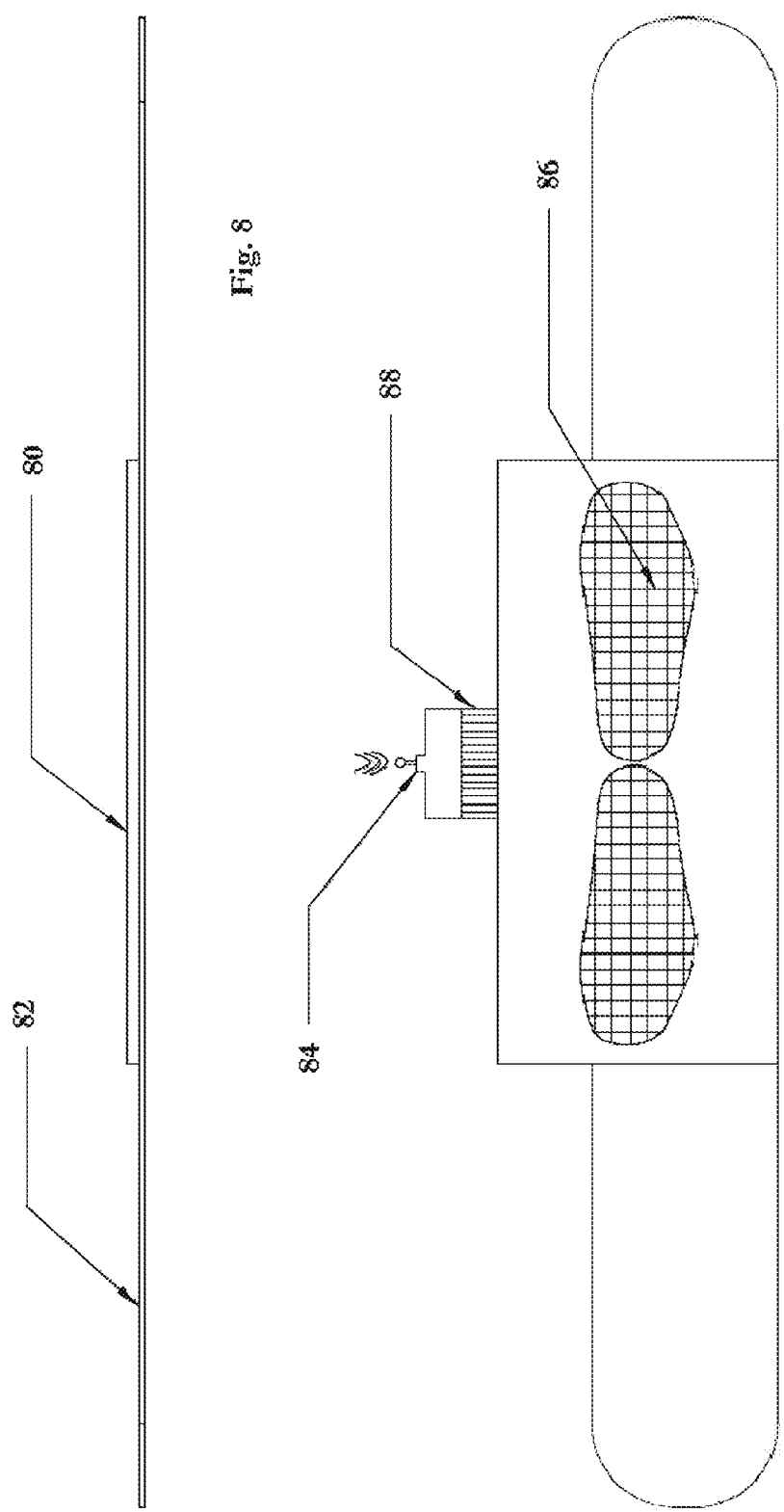

PERIPHERAL SENSORY AND SUPERSENSORY REPLACEMENT SYSTEM

CROSS-REFERENCE TO RELATED APPLICATIONS

This application is based upon and claims the benefit of priority under 35 U.S.C. § 119(e)(1) from U.S. Provisional Application No. 61/408,373, filed Oct. 29, 2010, the entire contents of which are herein incorporated by reference.

BACKGROUND

A peripheral sensory and "supersensory" quantification, replacement, augmentation and analysis system is provided. More particularly, a data acquisition and transmission unit, a processing unit, and a receiving unit are provided. Some exemplary applications of the system include uses in healthcare, athletics, occupational health and safety and the military. Prominent healthcare uses include the management of peripheral neuropathy, lower extremity amputees and other rehabilitating patients.

Decreased or absent sensation resulting from peripheral neuropathy (or any other condition leading to inadequate sensation) leads to tremendous morbidity and poses a great challenge to the healthcare team caring for these patients. Sixty percent of peripheral neuropathy is secondary to Diabetes, with the remaining 40% being attributed to all other causes.

Nearly half of all diabetics will develop clinically significant peripheral neuropathy over the course of their lifetime; 25% are afflicted at any given point in time, and 7.5% of patients are symptomatic at the time of presentation. The vast majority of patients with peripheral neuropathy (of any cause) have a chronic, distal, symmetric polyneuropathy (i.e. decreased sensation in a stocking-and-glove distribution), affecting the nerves in a length-dependent fashion. Indeed, this prevalence data is thought to be skewed toward clinically relevant cases of peripheral neuropathy, and are likely somewhat underestimated. This prevalence data may be even further underestimated without the routine use of more sensitive methods of detection, including autonomic and quantitative sensory testing.

The prevalence of Diabetes in North America is 7%; nearly half of these patients ultimately have clinical courses complicated by peripheral neuropathy. The lifetime risk of a diabetic foot ulcer in these patients ranges from 15-25%, with a 2% annual incidence of ulceration. It has been estimated that 50% of all ulcers recur within 3 years, leading to further deleterious effects on patient quality of life and the health economy. Indeed, studies have shown that foot ulcers cause substantial emotional, physical, productivity, and financial losses. What is more, Diabetic Foot Syndrome (DFS) precedes 84% of all lower extremity amputations. In terms of the associated economic burden, the cost of treating a single diabetic foot ulcer (not factoring in recurrence) ranges from $18-$28,000 CDN, and approaches $35-50,000 CDN when the end result is amputation.

The consequences of peripheral neuropathy are manifold. First, this loss of protective sensation leads inadequate plantar feedback and therefore unchecked pressure distribution, leading to focal ischemia, pressure necrosis, ulceration, and then finally, infection and gangrene. Second, impaired sensation leads to balance dysfunction ("mal-equilibrioception") and subsequent gait and mobility issues. Normal equilibrioception results from a coordination of visual, vestibular, and tactile/proprioceptive (predominantly plantar) inputs. While some variation exists between individuals, humans typically require two intact systems to achieve normal balance perception. In addition to the balance issues posed by decreased peripheral sensation, the lack of real-time feedback of when the plantar surface is on (and when it is elevated off of) the ground surface has further deleterious effects on mobility, often resulting in a slow, unsure and shuffling gait, and increased potential for falls.

These sensory, balance and gait concerns also apply to lower extremity amputees (users of prosthetic limbs) and other rehab sectors. In North America, it is estimated that 1 in 200 people are living with a lower extremity amputation, with these estimates expected to more than double by 2050. At present, this equates to over 1.7 million people. Indications for such amputation include severe ischemic disease of the lower extremity, traumatic mangling, tumor resection, infection, congenital limb deficiency, vascular compromise, and infection (often a consequence of severe pressure-induced diabetic ulceration). Following amputation, patients have problems with both care of the amputation stump, as well as their prosthesis. He or she must learn to apply, walk with, remove and care for the prosthesis; he or she must also monitor the stump skin for any pressure points, and ambulate on difficult terrain (in both light and dark) with inadequate sensory feedback from both the stump and the sole of the prosthesis. Resulting problems include stump damage, infection, further amputation and death, as well as issues with walking, balance and potential falls.

BRIEF SUMMARY

Previous work in plantar pressure monitoring for the purposes of sensory substitution has used a plantar pressure data acquisition system to simply look at a center of foot position for people with balance issues. The system has "threshold alarm" feedback for center of foot position, that alerts the user with an electrical impulse on the tongue, when the foot is displaced from a normal, balanced stance. These outdated systems (which are only experimental and are not commercially available) do not provide the user with continuous, real-time feedback of differential pressures over the entire plantar surface, or of specific components of interest on the lower extremity as a whole.

Further, prior systems use sensors that require more power, which limit usability and commercialization potential. The only pressure-sensing insole developed to date that has been made commercially available (albeit mostly to institutions for research purposes) is the "F-Scan" system (by Tekscan). This system takes in large number of pressure inputs. Because of the volume of input data, it is not easily transmitted wirelessly, rendering the device to a cumbersome, wired system. No commercially available, user-friendly, wireless pressure-sensing insole has ever been developed and commercialized.

Patients rehabilitating from strokes would benefit from such a device. The lifetime risk of stroke is 1 in 6. Of the 85% of people who go on to survive their stroke, nearly 10% (4.8 million) experience long-term gait disturbance and related rehabilitation needs. These sensory feedback requirements are met with the inventor's proposed system.

Outside of healthcare, the system has extensive applications in athletics and activity monitoring and optimization, including individual and group tracking, team dynamic analysis, quantification of kinetics and kinematics, performance quantification, compliance assessment and activity mapping.

Military applications include the development of sensory replacement and augmentation systems for the purposes of detection of, and alerting the user to, pertinent environmental features and imminent danger (including, but not limited to sensing methods involving detection of: TNT, landmines, foreign bodies, heat (infrared), radiation (Geiger), sulphur dioxide, and other chemicals of interest).

Occupational Health and Safety applications include the exemplary case of a lower extremity-based device that is used to detect (and alert the user or employee to) situations of over-lifting or improper lifting. This force and kinetics/kinematics application also has uses in healthcare monitoring (in rehabilitating, users of prosthetics, and diabetic, cardiac, obese, post-cancer and post-operative patients, for example).

In one example, a sensor-based quantification and analysis system includes an input device including a plurality of sensors that generate an input based on a force. The input device also includes a transmission device that transmits force information based on the input. Further, the system includes an output device that receives the force information. A processing unit selects, for each of the plurality of sensors, one of a plurality of levels of a likelihood of tissue damage based on the force and a predetermined time period. In addition, the output device includes a display that presents or logs the one of the plurality of levels of the likelihood of tissue damage for each of the plurality of sensors.

The input device optionally includes a sensor that senses supersensory data. The transmission device optionally transmits supersensory information based on the supersensory data to the output device. The display optionally presents or logs feedback data based on the supersensory information.

The display preferably presents the one of the plurality of levels of the likelihood of tissue damage using at least one of a visual display and a tactile display.

In one example, the display presents the one of the plurality of levels of the likelihood of tissue damage using the tactile display. The tactile display is at least one of electro-tactile, vibro-tactile, and temperature-tactile. The tactile display is affixed to a back.

In a further example, the tactile display is arranged to provide a neuroplastic effect.

The display preferably logs and stores the one of the plurality of levels of the likelihood of tissue damage remotely from the input device.

In one aspect, the display presents the one of the plurality of levels of the likelihood of tissue damage using an auditory method.

The display preferably includes a visual output unit that displays a plurality of areas corresponding to locations of the plurality of sensors.

The output device preferably includes a wristband.

In another aspect, the input device includes a temperature sensor and a moisture sensor. The transmission device transmits information based on a temperature sensed by the temperature sensor and a moisture sensed by the moisture sensor. The display presents information based on the temperature and the moisture.

In a further aspect, the processing unit is located in at least one of the input device and the output device.

In another example, a sensor-based quantification and analysis system includes an input device including a plurality of means for generating an input based on a force. The input device also includes means for transmitting force information based on the input. The system further includes an output device that receives the force information. The system also includes a means for selecting, for each of the plurality of means for generating, one of a plurality of levels of a likelihood of tissue damage based on the force and a predetermined time period. The output device includes display means that present or log the one of the plurality of levels of the likelihood of tissue damage for each of the plurality of means for generating.

In a further example, a quantification and analysis method includes generating an input based on a force, using a plurality of sensors. The method also includes transmitting force information based on the input, and receiving the force information. In addition, the method includes selecting, for each of the plurality of sensors, one of a plurality of levels of a likelihood of tissue damage based on the force and a predetermined time period. Further, the method includes presenting or logging the one of the plurality of levels of the likelihood of tissue damage for each of the plurality of sensors.

BRIEF DESCRIPTION OF THE SEVERAL VIEWS OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3 illustrates an example input device (multiple views).

FIG. 7 illustrates an example output device (multiple views).

FIG. 8 illustrates another example output devices (multiple views).

DETAILED DESCRIPTION OF THE PREFERRED EMBODIMENTS

In the management of peripheral neuropathy, the current gold standard of care includes primary prevention via diabetes education and prescription of traditional orthotic insoles. Beyond this, reactionary wound care and ulcer/infection control is the standard of care. This is an outdated approach applying principles of sickcare, not preventative healthcare that the present system offers. Further, in terms of economics, the present system carries huge potential savings for both the patient and the healthcare system, detailed as follows.

Figure 1:
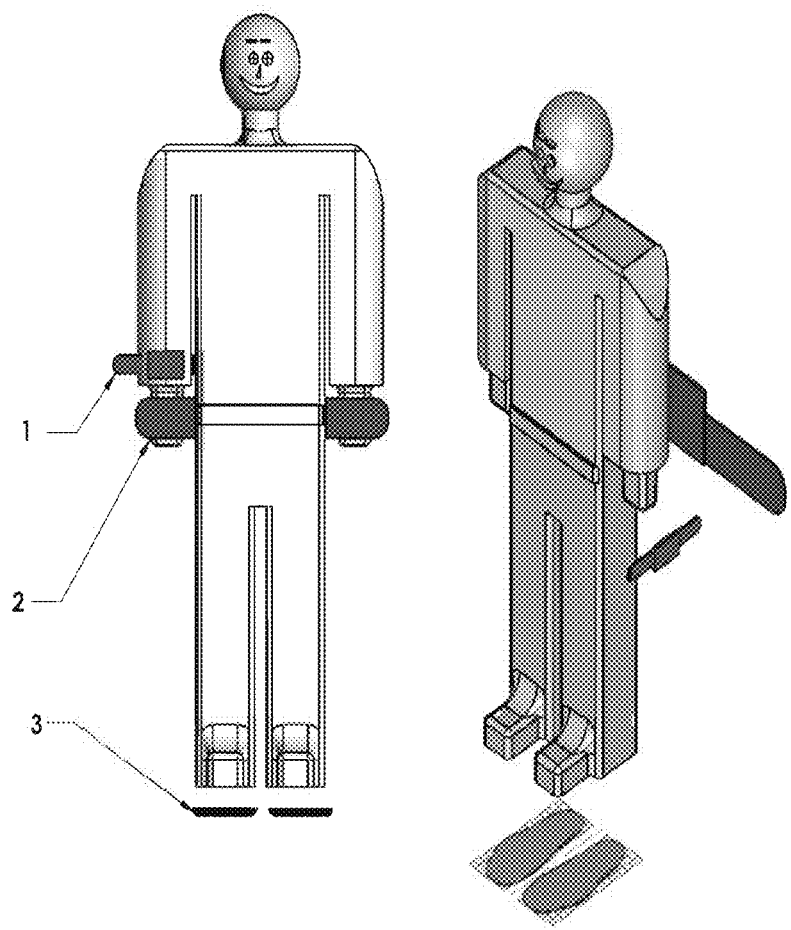
FIG. 1 illustrates an example of a system including an input device and a receiving device.

FIG. 1 shows an exemplary system employing two parts: an input device, such as the input device 3, which will receive and transmit pressure readings from across a foot; and a receiving device, such as the wristband 1 or a back display 2.

Figure 2:
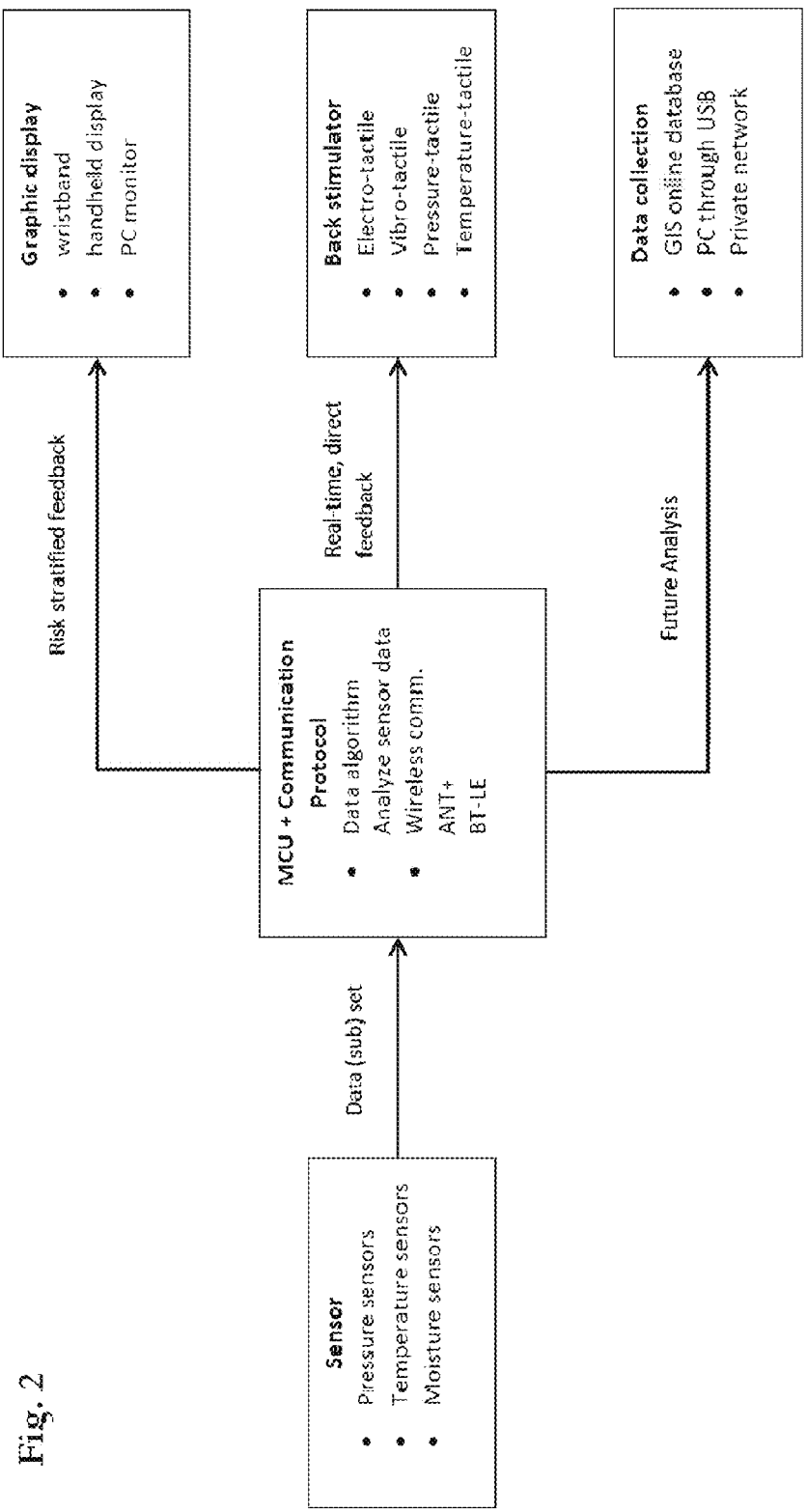
FIG. 2 illustrates a schematic diagram of the system.

In one exemplary aspect shown in FIG. 2, an input device designed to record pressures along the bottom of the foot is provided. In one example, the input device is an insole. Via a communication system, the pressure data is sent to one of a series of potential receiving devices, such as a specially designed wristwatch, described in greater detail below.

As also described in greater detail below, the communication system may be based on a wireless communication, and is therefore able to interact with a whole host of devices for ease of information transfer and/or personal health monitoring. Potential receiving devices include (but are not limited to) wristwatches, USB keys, enabled dongles, cellular telephones and personal laptops.

Another potential receiving device is a stimulator designed to be worn on the back, described in greater detail below, which will thus send a stimulus, in the form of a display (in the form of an electrotactile, electrotextile, vibrotactile, chemotactile, temperature- and/or pressure-mediated stimulus) to the user. The sensate skin of the back will receive the stimulus, and through the phenomenon of neural plasticity, the user—with enough practice—may learn to interpret the stimulus as input from the foot. Together with the input device, this receiving device creates a sensory replacement or augmentation system.

Further, in one example, the receiving device is made to contain software for data requisition. Thus, in the example of the back display, the data requisition software is engineered to transmit data in the form of a real-time, differential electrical impulse over the embedded stimulators in the back display.

The system described herein can be advantageously employed for the prevention and treatment of pressure-related diabetic foot disease (e.g. balance and gait issues, ulceration, infection, and amputation). Other uses include applications in patient rehabilitation (amputation- and stroke-related, for example), athletic and/or activity monitoring, military and OH&S uses. The sensors can be embedded in a custom- or generic-made insole, for example. The data acquired by the system can be used for custom-made, pressure-relieving foot orthotics, as well as for relay of pressure status to the patient/user or a third party (including healthcare practitioners). In addition, the system can be used to improve gait and balance in patients with decreased/absent plantar sensation (e.g. patients with peripheral neuropathy and/or lower extremity amputation), or to assist an athlete in optimizing foot and ankle manipulation, or, in general, their kinetics and kinematics.

Other aspects of the system include the inclusion of further diagnostic sensors and algorithms, enabling the device to measure aspects such as: GPS, heart rate, respiratory rate, blood pressure, temperature, blood oxygen saturation, blood flow, blood or environmental content quantification (e.g. glucose, electrolytes, minerals, oxygen, carbon dioxide, carbon monoxide, HbA1C, Ethanol, protein, lipid, carbohydrate, cortisol, lactate, pH, pro- and anti-inflammatory markers, MMPs, Growth Factors, bacterial content), hydration status/tissue turgor, joint position, features of gait analysis (including supination and pronation), device breakdown, pedometry, accelerometry, velocity, calorimetry, centre of gravity or centre of foot position, friction, traction, contact area, connectivity/insulation, EEG data, and/or ECG data. These sensors can be placed within a pressure sensor (or other sensor) grid of the input device in, for example, a checkerboard pattern. An example of a laser blood flowmeter is described in, for example, U.S. Pat. No. 6,944,494, entitled "Motion Measuring Device," issued Sep. 13, 2005, the entire contents of which are hereby incorporated by reference. In one example, the input device comprises multiple devices, located at different anatomic (or extra-corporeal) locations on one or many individuals or objects. In another example, the output system comprises multiple devices, located at different anatomic (or extra-corporeal) locations on one or many individuals or objects. In different examples, the input and output devices can be the same or different devices.

In addition, the pressure sensor technology of this system can be applied to help prevent and manage pressure ulcers on various parts of the body, including (but not limited to) the foot, leg, buttock, sacrum, back, elbow, shoulder/scapula and scalp. The technology may also be used to enable tactile feedback in robotic surgery and applications related to surgical (and other forms of tactile- or sensor-based) education.

The present system can be used to prevent and treat Diabetic Foot Disease, and improve gait and balance issues in patients with decreased or absent plantar sensory feedback.

Advantageously, the present system has a low-profile, ergonomic, user-friendly device utilizing ultra-low power consumption, provides improved quality of life for the users of the device, has potential for cost-effectiveness and global healthcare system savings, and may employ state-of-the-art wireless technology and innovative materials. The low profile and ergonomic features of the stimulator are derived from the use of light and thin sensors/stimulators. Low power can be achieved through the choice of wireless communication protocol, type of sensor and stimulator as well as the chipset and electronics used.

I. Input Device(s)

Preferred input devices include any foot-based system (e.g. insoles, shoes/boots, casts, lower limb prostheses, pads that can be adhered to the bottom of an amputation stump, etc.), and any hand-based system (e.g. gloves, mitts). Beyond these peripherally attached devices, other inputs of interest would be developed with the intention of preventing other common areas for pressure ulcer development (e.g. clothing or mats to detect when the patient is at risk of developing buttock, sacral, ischial, scapular, and scalp ulceration). Further, the present system can be realized in, but is not limited to, lone sensors (that are adhesive and/or bandage based, for example), anklets, air-casts, splints, prosthetics and dressings themselves.

FIG. 3 illustrates one exemplary embodiment of the input device. An insole containing an array 11 of embedded pressure or force sensors for monitoring of pressure or force distribution (real-time or sporadic) over the bottom of the foot is provided. The array of pressure sensors can be distributed over, and laminated within, an upper surface 12 of a low compression, polyurethane insole that is made of a resiliently flexible material that is designed to fit in a shoe. The pressure sensors are, for example, low power piezo-electric or piezoresistive capacitive sensors. In one example, the pressure sensors are A401 FlexiForce sensors produced by Tekscan, Inc. of South Boston, Mass.

Contained within the insole bulk, or an affixed device, is a wireless transmission node 13 designed for integration and transmission of, for example, a 4 Hz wireless sigal containing "real-time" or sporadic information pertaining to pressure or force distribution (or any other measure other input) from the foot or ther anatomic location, including—but not limited to—the sole. The array 11 of pressure sensors communicate with the wireless tracsmission code 13 via a ribbon cable 14. The input device , as well as the other devices described herein can employ a low power chipset that is run by a real-time operating system (RTOS), which enables communication through low power wired or wireless protocols, such as, but not litited to ANT+®, ZIGBEE®, Gazelle, BLUETOOTH® and BLUETOOTH LE® protocols.

Under the array 11 of pressure sensors, a cushion layer 15 is provided. Under the cushion layer 15, a support layer 16 is provided. In some embodiments, the support layer extends from the heel to the toes. Alternatively, the support layer extends merely from the heel to the arch.

The input device is not limited to the configuration illustrated in FIG. 3. For example, generic, formed or flat, or custom orthotic insole designs are all possible. A low-profile model is a flat, 2D, low-profile insole based of polyurethane, for example. Formed models (which may be generic or custom made) may be polyurethane-based, and are three-dimensional molded insoles designed to realign the lower limb with added arch support, with emphasis in design on improving foot function, and relieving associated heel, ankle and limb pain by reducing excess pressure on, as well as pronation and supination of, the foot, or other specific needs of the patient/user. This insole is may be based on pressure data acquired from a patient-specific gait analysis. In some embodiments, the insole is fashioned to support the shape of the foot, whereas in other embodiments, the insole is fashioned as a flat, non-supportive structure.

Figure 4:
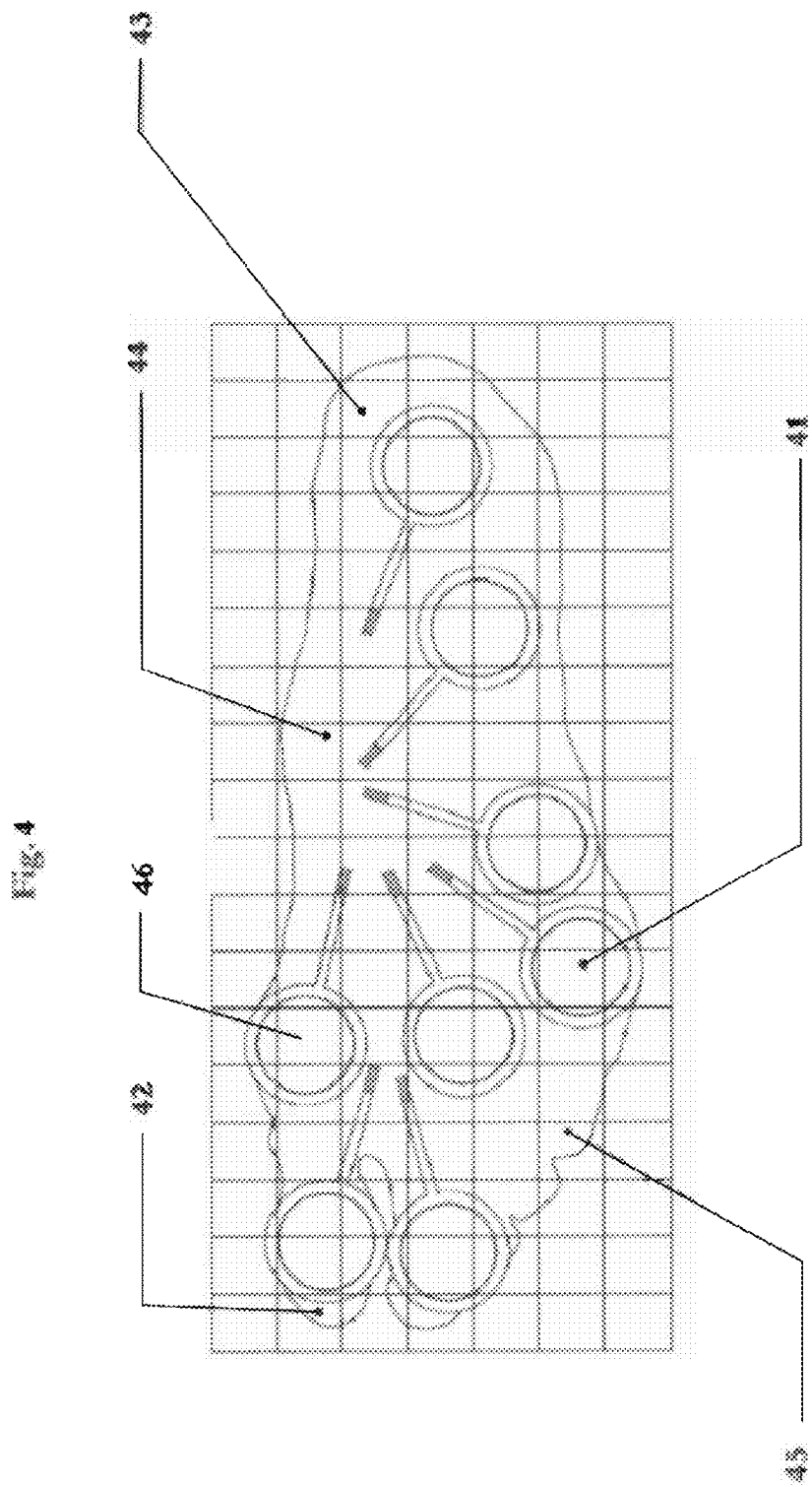
FIG. 4 illustrates an exemplary positioning of an array of sensors.

FIG. 4 shows an example in which the sensors 41 are placed in the insole strategically. The present inventors recognize that different areas of the foot have different risk categories. For example, the higher risk areas of the foot are based on bony prominences and foot biomechanics. The highest area of risk is the first metatarsal-phalangeal (MTP) joint 46. Other key areas are the other MTP joints, the toes (such as great toe 42), the heel 43 and the lateral side of the foot.

Further, pressure sensors are of more use when located at areas in the insole corresponding to pressure points (bony prominences) in the foot, where safe pressure thresholds are more likely to be exceeded.

Thus, in one example, the sensors are placed at locations corresponding to bony prominences (pressure points) in the feet, which will not change for generic types of input devices, such as insoles. FIG. 4 shows some of the sensor locations relative to an arch 44 of the foot and the small toe 45. For custom fit types of input devices, depending on abnormalities in the shape of the individual's foot, the sensors may be placed in different locations.

The insole contains embedded (or affixed on a wired or wireless basis) software to receive the pressure or force data from the sensors. The embedded (or affixed on a wired or wireless basis) software differentially maps the pressure in an insole, for example, for use in a pressure or force sensing, monitoring, analysis, feedback and/or therapeutic system. This information may be analyzed by a processing unit, described below, in either the input or receiving device. As shown in FIG. 3, a layout of spaced-apart pressure sensors is embedded in the insole, each of which has a predetermined height and diameter. The input device provides a real-time pressure or force (or other input) map of the body part being measured: in this example, the sole of the foot. When mapping the pressure or force incurred over the insole, recordings from each sensor can be differentially received as a function of time. Also, in the present example, the system will record the broad range of pressures or forces (or other sensor-based inputs) encountered anatomically or physiologically or by an outside body (animate or inanimate).

Depending on the output device described below, the density and location of the sensors will vary somewhat. In examples focusing on simpler output units (e.g. the wristband), sensors will only be placed at high-risk locations, such as bony prominences. In an embodiment including a back display, there is a high density of sensors (likely in the range of one sensor per square centimeter) so that the sensory substitution felt through the back is of a higher resolution, and essentially a "map" of the sole, not just discrete points of concern.

Figure 5:
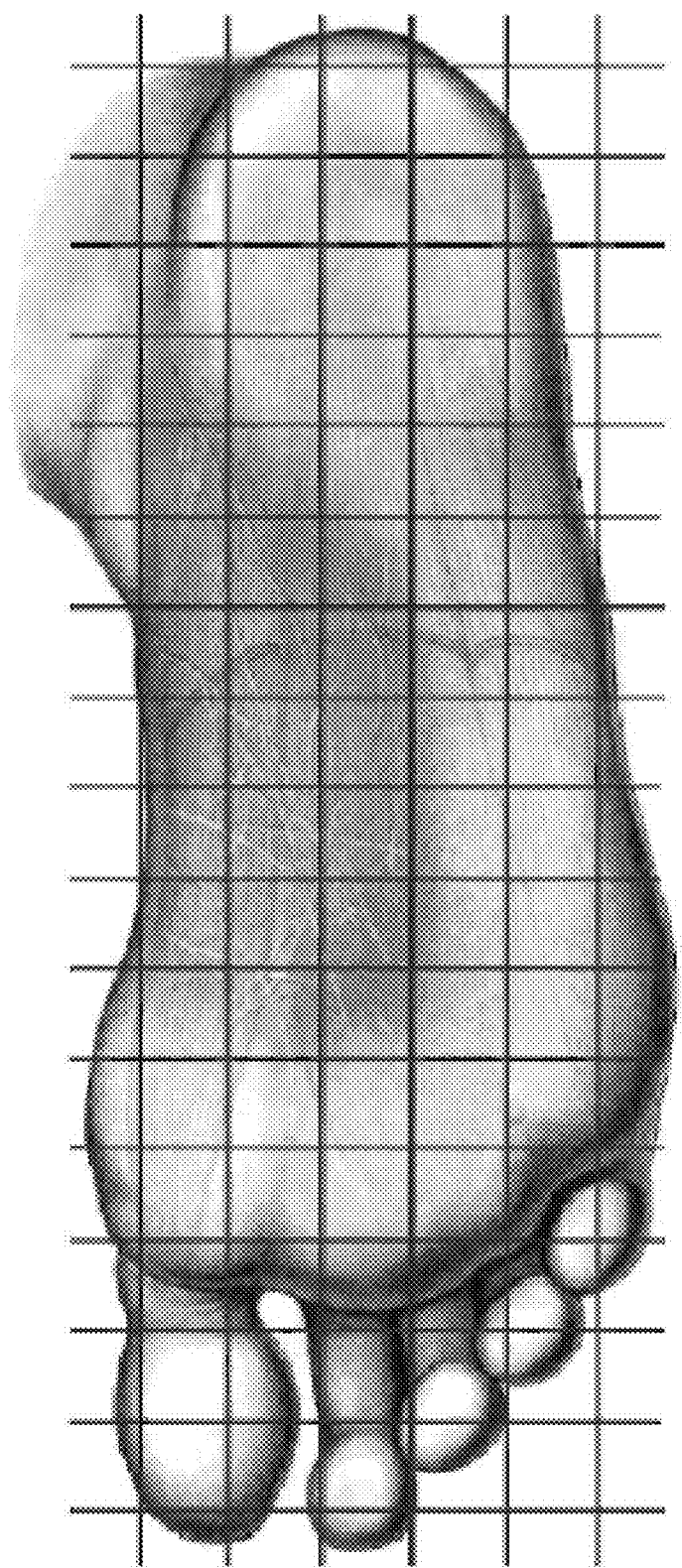
FIG. 5 illustrates another exemplary positioning of an array of sensors.

As illustrated in 4 and 5, the number of sensors are varied to achieve different levels of resolution. For example, FIG. 4 illustrates an option with eight strategically placed sensors per insole, and FIG. 5 illustrates a high-resolution option containing one sensor per regular area, e.g., per square centimeter, over the entire surface of the insole. The eight pressure sensors in FIG. 4 are located such that each correspond to an area most prone to ulceration (two sensors over the toes, three across the five MTP joints, two along the lateral plantar foot and one on the heel of the foot). The example in FIG. 5 contains pressure sensors at each regular interval over the surface of the insole and conveys information from the entire plantar surface. Thus, the example in FIG. 5 is more effective with respect to ulcer prevention and plantar sensory replacement or augmentation.

In addition to incorporating the input device into an insole, the use of thin, low-profile pressure (or other) sensors also allow the input device to be realized as a sock, or other article of clothing. In the above-described embodiment, the insole is removable from a shoe. However, it is also contemplated that the insole is part of a shoe, or that the said insole is part of a sock. Likewise, the pressure sensors can extend over a variable area within the shoe or the sock.

Realizing the input device as a sock or shoe is preferable, in that such a device gives greater coverage than merely the sole of the foot. In such an example, the sensor location can change to non-plantar surfaces. As discussed above, the location and density of pressure sensors depend on the output device being used. If the output device is based on a wristband output, there would be fewer sensors at key locations.

Modifications can include additional sensors (to detect, for example, TNT). If a sensor has been included to detect an environmental danger (e.g. in the case of TNT detection), then the sensor would be placed in a location external to the article of clothing itself.

While a whole host of sensors may be included, additional sensors of particular preference are: temperature, moisture, blood flow and blood glucose sensors. Pressure aside, these are the major potential impediments to the healing of diabetic wounds.

In the case of sensors incorporated to measure physiological phenomenon (e.g. blood glucose level), those sensors would need to be located in proximity to the skin interface. Some sensors, like temperature sensors, are unique in that they may be located within the article of clothing itself or external to it, depending on whether the external environment or the user's body temperature/immediate skin interface temperature are of interest.

Environmental temperature sensors, for example, would be more useful when incorporated into the part of the insole corresponding to the forefoot. The reason for this is that in diabetics (a group who commonly burns their feet unknowingly), the area of the foot most likely to come in contact with hot environments/flame is the front of the foot; temperature sensors placed at the forefoot would more efficiently diagnose an unsafe environment.

Environmental temperature sensors embedded with the aim of identifying "danger" zones (e.g. flames) would be located at or near the skin itself. The temperature of this area would be the primary point of concern, whether or not the user's own body heat impacted that measurement.

In the case of a system in which the sensor has been included to measure body temperature itself, there will likely be more than one temperature sensor, and this would be located most strategically to avoid having external temperature conditions impact that measurement (e.g. not placed near the forefoot).

In the case of sensors intended to measure blood flow and content-related sensors, these may most appropriately be located in anatomic areas with superficial blood vessels (e.g. the dorsum of the foot or around the medial aspect of the ankle).

Sensors can also be located in non-plantar aspects of the shoe. In addition, for non-foot-based applications, the input device may be contained in a direct contact sensor (applied by an adhesive or band, for example), any article of clothing (gloves, shirts, undergarments, hats, belts, watches, necklaces), or a blanket or pad that may be placed on any anatomic location of interest.

Therapeutic technologies may be incorporated in the input device, including a transcutaneous electrical nerve stimulation (TENS) unit (for example, for developed ulcers on the foot), and capabilities for temperature, moisture and/or pressure/force auto-adjustment. For devices that employ such therapeutic modalities, these can also be on an overlay pattern with sensors.

II. Communication Device

The system of the present disclosure has extensive applications, depending on the input device and receiving device that the input device is "talking" to via a communication system. In one exemplary case, the communication system is a low-profile, low energy wireless protocol. The communication system could comprise any wired and/or wireless, fibre optic, or human circuit. In the wireless example, the information can be variously transmitted to an output device, such as a wristwatch, a cellular phone, a USB key, a dongle, a personal laptop computer, or a sensory replacement or augmentation system, which will be described in greater detail below.

Pressure or force (or other sensor-based) data from the input device can be transmitted via a low-profile, ultra-low energy wireless protocol to an output device, such as a wristband.

An input device, such as the foot pod, will simply broadcast data. If a receiver is within range it will acquire the signal and do a "handshake" to sync its respective RF antenna.

III. Processing Device

The processing device may be included in the previously described input device, the later described output device, or any other device in the system.

The processing device in one exemplary aspect of the present disclosure employs a system that does provide the user with continuous, real-time feedback of differential pressures over the entire plantar surface. The inventors have found this to be particularly beneficial, as gait is a dynamic exercise employing constant feedback from the plantar sole, and the potential for neural plasticity would theoretically be maximized with a biofeedback loop that projects an output that more closely resembles the native, deficient sense. Additionally, the real-time, differential pressure system can provide the user with information about texture and foreign object location. A rock under a discrete aspect on the foot, for example, may not be appreciated with the aforementioned experimental system.

Figure 6:
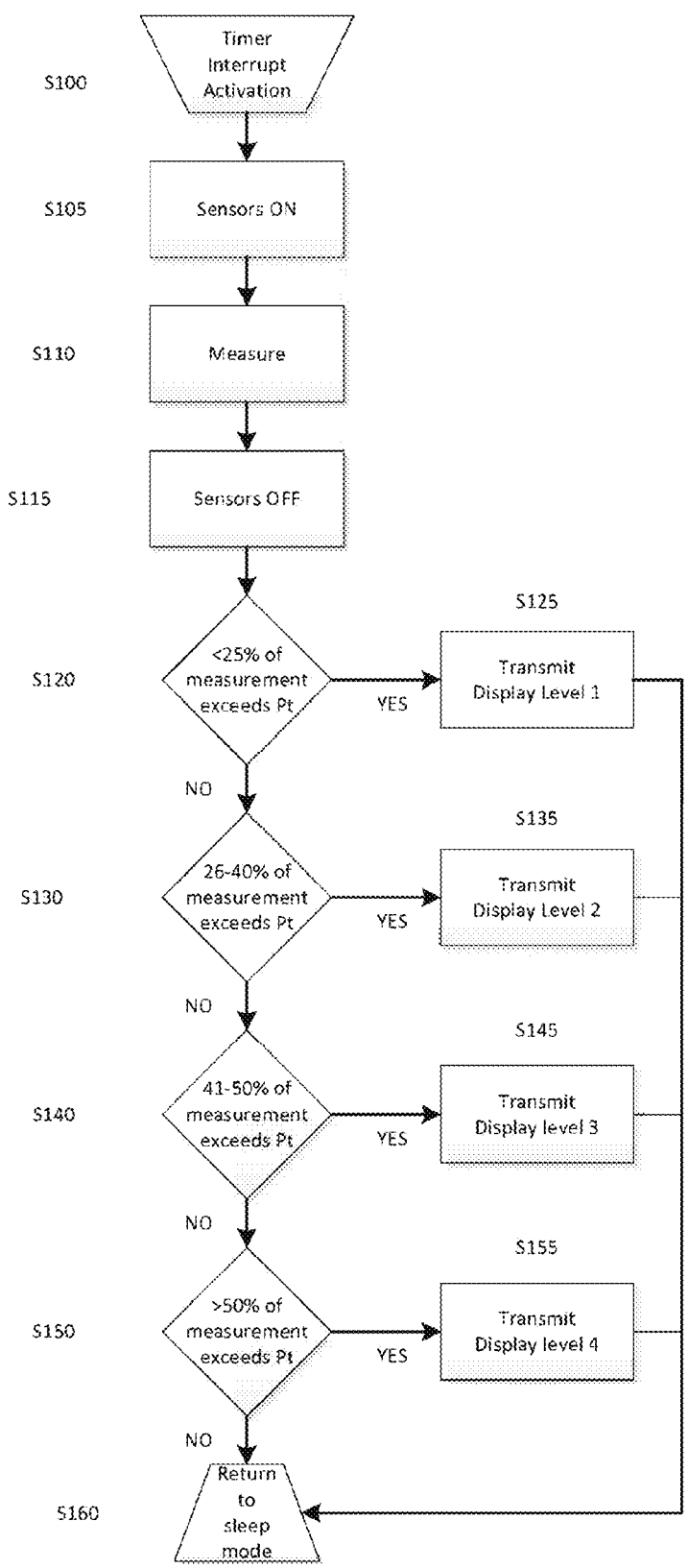
FIG. 6 illustrates an exemplary algorithmic processing performed by a processing device.

FIG. 6 shows an exemplary algorithm for a pressure sensor data conversion to display scale. The algorithm begins at step S100, at which the array of sensors receives a timer interrupt activation. The array of sensors are then turned on at step S105. At step S110, the sensors perform a measurement. In a preferred embodiment, the performed measurement measures a force or pressure. In further preferred embodiment, a humidity or temperature is measured. At step S115, the sensors are turned off.

The processing device then performs a stratification of a likelihood of tissue damage, letting Pt=pressure threshold (approx. 30 mmHg).

In one example, the likelihood of tissue damage is stratified into four levels. In that example, Level 1 corresponds to less than 25% of pressure measurements exceeding Pt, within a 15 minute time frame. Thus, at step S120, the processing device determines whether 25% of the measurements within the 15 minute time frame exceed Pt. If so, the algorithm proceeds to step S125, where a signal indicating display level 1 is transmitted. If not, the processing device determines at step S130 whether 26-40% of the pressure measurements exceed Pt, within a 15 minute time frame. If so, the algorithm proceeds to step S135, where a signal indicating display level 2 is transmitted. If not, the processing device determines at step S140 whether 41-50% of the pressure measurements exceed Pt, within a 15 minute time frame. If so, the algorithm proceeds to step S145, where a signal indicating display level 3 is transmitted. If not, the processing device determines at step S150 whether more than 50% of the pressure measurements exceed Pt, within a 15 minute time frame. If so, the algorithm proceeds to step S155, where a signal indicating display level 4 is transmitted. If not, the algorithm proceeds to step S160. These signal transmissions can be sent to an output device by a wireless communication, for example. In embodiments in which the processing device is internal to an output device, the signal can be sent within the output device to, for example, a visual display unit. In any case, after the signal transmissions, the algorithm proceeds to step S160.

At step S160, the sensors return to sleep mode. The algorithm then ends.

If a sensor measures the pressure at 4 Hz, then within 15 minutes a total of 3600 measurements are taken. Thus, if a sensor corresponding to a region L1 as shown in the drawings measures that more than 1800 out of 3600 measurements is above the pressure threshold, the processing device generates a signal so that a the output device generates an alert for region L1 on the display. Measurements exceeding the threshold do not have to be consecutive in order to cause an alert.

When using multiple sensors in single region, the sensor with the highest value will dictate what the processing device determines. Thus, if any sensor in a region is high, then the processing device will generate a signal for the output device, in which the whole region lights up.

Further, key principles in the management of diabetic foot ulcers include the adherence to the principles of good wound care, such as adequate offloading of pressure, prompt treatment of infection, and moist wound dressings (while avoiding maceration from over-moisture). Taken together, this information lends that a system measuring combinations of moisture, temperature, bacterial load and pressure would be more comprehensive for the care of the diabetic or neuropathic foot than a system which only measures one of these aspects of optimal care. Thus, one embodiment includes a plurality of moisture, temperature, and bacterial load sensors that provide information to the processing device. The processing device then makes a determination based on the information received from those sensors.

Beyond this, the inventors are aware that temperature differences of >4 F (>2.2 C) between a plantar site and other plantar sites is an early indicator of impending ulceration. Thus, in an embodiment in which the input device includes multiple temperature sensors, the processing device provides an additional alert to the output device if the temperature difference between two of the temperature sensors exceeds 4 degrees Fahrenheit.

If the measurement frequency increases (i.e. 10 Hz), the percentage would remain the same, however the software algorithm would be slightly modified as more measurements would be compared to the pressure threshold within the previous 15 minute time frame. The 15 minute time frame shifts with the passage of time, which allows for continuous monitoring.

Further, the processing of the analog (raw) sensor output will change if the sensors are located within the shoe. The processing will depend on 1) the biomechanics of the device that the sensor is embedded in; and 2) the subsequent effects those biomechanics have on the raw pressure output.

The processing device may determine that a foreign object, such as a rock, is in a shoe as follows. If the foreign object is creating a localized pressure increase, the processing device will generate a signal for the display, if the sensor exceeds the threshold for more than a number of readings taken at a standardized frequency. The signal will alert the user to inspect the shoe.

Further, when walking, a sensor might inappropriately trip the processing device's alarm threshold. Therefore, the processing device requires several trips of the sensor, such as the percentage of pressure measurements described above. This stratification takes into account a user's cadence, particularly when running.

Further, the processing device will be able to also count steps/impact, and from that, cadence can be determined.

The processing device can also control the sensors to turn off when no readings are received within a predetermined time. The device will go into sleep mode between measurements at a predetermined time interval. The watch will not go into sleep mode unless it is instructed (e.g., button on watch) or both insoles are out of range. If for example, the left insole is malfunctioning or out of range, the processing device can generate a signal for the display to alert the user of this fact.

Neuropathy-related applications are concerned with identifying situations in which a pressure threshold as a function of time (e.g. several minutes) has been exceeded. The pressure threshold in this situation is relatively low; an alert-able scenario would be one in which even small pressure measurements have been seen (and not offloaded) over the course of a relatively longer period of time.

In Occupational Health and Safety contexts, the data from the sensors will be processed by the processing device differently, depending on the application. For example, in the case of OH&S applications intended to identify "overlifting," the analysis of the data is done in a way to identify situations in which a relatively higher pressure threshold has been exceeded over a short time period (a single or few-point frame of time).

Further, in a pressure/force auto-adjustment, a pressure-sensing insole may incorporate the capability to "auto-adjust." Say, for example, the wearer had exceeded (or was at risk for exceeding) a safe pressure threshold over the right first metatarsal head. The insole would have incorporated within it the intrinsic capability to re-form in such a way that pressure would be redistributed, and the area of concern would be offloaded. An example of accomplishing this would be by way of an insole with discrete air pockets that would auto-inflate or deflate to accomplish the immediate needs of the user by way of a processing device output.

Modified systems also incorporating this principle of auto-adjustment have ample utility in pressure sore prevention of other forms (e.g. circumvention of sacral ulcer development in bed- and wheelchair-ridden patients).

It is also possible to update various thresholds (e.g., pressure, duration, sensor activation, actuator activation).

IV. Output Device

The system of the present disclosure encompasses a series of solutions for sensory replacement, augmentation and analysis. For example, potential output devices for use with the input device include clothing, wristbands, laptop computers, USB sticks, dongles, cellular or smartphones, televisions, web-based applications, other displays (including, but not limited to, LCD displays), back displays and heads-up display devices, such as those manufactured by 4iiii™. When relaying data via stimulation, these may be located on the body of interest and/or a different body.

Depending on the application, one output device will be preferable over another. The three most preferable exemplary output devices are: 1) an LCD display; 2) a back display; and 3) a USB key (or other method of directly uploading data to a central location).

The LCD display is most useful in the situation of a diabetic patient (or other patient with peripheral neuropathy), who wishes to be simply alerted to situations in which damage may be done. This encompasses any patient with a fear of, and therefore a wish to mitigate the risk of, developing pressure-related damage.

The back display feedback device will be preferable for rehabilitation applications, as the patient will be able to have real-time direct feedback, and substitute sensation for that which he or she is deficient in. The same goes for any patient with: a) dense peripheral neuropathy; and/or b) a desire to "feel" the bottom of a prosthesis (e.g. the foot component).

The USB key (or other method of directly uploading data to a central location) output device is most applicable for the collection and analysis of the data by either a third party (e.g. physician) or future analysis by the patient him- or herself (e.g. viewing graphs of pressure encountered over time).

In one example of the LCD display, illustrated in FIG. 7, a wristband 70 includes the LCD display 72, which is designed to display both graphical and numerical data pertaining to pressure or force incurred on the bottom of the foot. The LCD display also includes a node 76 for receiving wireless data signals. The wristband can be, for example, a digital timepiece provided with a quartz oscillator, frequency divider and counting circuits, a decoder and a digital electro-optical display device. In addition to the functions described above, the timepiece can be suitable to operate as a standard digital wristwatch to display time data. The wristband can also display data received wirelessly from another device, including: GPS, heart rate, respiratory rate, blood pressure, temperature, blood oxygen saturation, blood flow, blood or environmental content quantification (e.g. glucose, electrolytes, minerals, oxygen, carbon dioxide, carbon monoxide, HbA1C, Ethanol, protein, lipid, carbohydrate, cortisol, lactate, pH, pro- and anti-inflammatory markers, MMPs, Growth Factors, bacterial content), hydration status/tissue turgor, joint position, features of gait analysis (including supination, pronation), device breakdown, pedometry, accelerometry, velocity, calorimetry, centre of gravity or centre of foot position, friction, traction, contact area, connectivity/insulation, EEG data, and/or ECG data. In addition, the data received from the input device may be stored and/or uploaded.

As discussed above, temperature, moisture, blood flow and blood glucose displays would be preferred, as these are the major potential impediments to the healing of diabetic wounds.

The wristband may also display other sensor data, such as temperature, moisture, and GPS status. Together, these measurements would give a more comprehensive view of the status of the foot. The GPS function, in particular, would enable tracking with respect to both patient activity compliance and/or athletic monitoring.

Because different areas of the foot have different risk categories, in the wristwatch face, a representation of each sole is divided into 7 areas (L1-L7 and R1-R7). These represent areas that act as different functional units in biomechanics and kinematics of the feet.

Further, in some embodiments, the 7 areas track the placement of the sensors in the input device. For example, area L1 corresponds to the sensor underneath the second and third toes in FIG. 4. Area L2 corresponds to the sensor underneath the great toe 41. Area L4 corresponds to the first MTP joint, and area L3 corresponds to the two other sensors along the other MTP joints, as shown in FIG. 4. Area L5 corresponds to the two sensors along the lateral foot between the MTP joints and the heel. Area L6 corresponds to an arch of the foot, whose sensors are not shown in FIG. 4. Area L7 corresponds to the sensor at the heel of FIG. 4.

In output device embodiments in which the input device sensors are located as shown in FIG. 5, the output device includes areas corresponding to the location of each sensor.

The device preferably displays at area 74 both graphical, auditory, vibrational and/or numerical data regarding the real-time pressures or other sensory data (such as temperature) encountered over the bottom of the foot. The wristband can be configured to display these outputs at the same time, or alone in different modes, for example.

A graphical display portion can include a reproduction of the outline of the feet (or other body part) with color (or grayscale) differentiation based on data from the input device. For example, on the graphical display portion, areas lighting up as green (or non-lit) refer to areas with low pressures that would be tolerated by the foot (or other body part) for any duration of time (e.g. <30 mmHg or Level 1). Areas lighting up as yellow (or grayscale) correspond to areas on the sole (or other body part) with pressures exceeding those tolerated (e.g. >30 mmHg), but that have been incurred for less than a specified time threshold (e.g. a 15 minute threshold or Level 2). Areas lighting up as red (or black or blinking) correspond to areas on the sole (or other body part) with pressures exceeding those tolerated (e.g. >30 mmHg), but that have been incurred for greater than the time threshold (or Levels 3 and/or 4). When that threshold is met, the wearer can be alerted via, for example, a visual, vibrational or auditory cue. The alert can subside once the pressure in question has been alleviated. For example, the color (or shading) will change from red (or dark or blinking) to green (or unlit) if a threshold for pressure offloading time has been reached. In addition to the red/yellow/green color scheme and grayscale discussed above, other schematic systems may be used, such as by using area 74.

In another aspect, as shown in FIG. 8, a display 80 mounted on the low back (or other anatomic location) of the patient is provided. In one embodiment, the display receives information for providing feedback to a user by way of a wired communication. In another example, the display receives wireless data signals via node 84. When the display receives data wirelessly, the data is provided to a display grid 86 by way of a ribbon cable 88.

This stimulating pad can transmit data to a user by an electrotactile, electrotextile, chemotactile, vibrotactile, pressure- or temperature-based output. The display can be affixed and held immobile to the area by way of a belt 82 worn around the mid-abdomen, or any other know means of adhering pads to the body that will be readily apparent to one of ordinary skill in the art. This device is more acceptable to patients than the previously described Tongue-Display Unit (TDU), as a patient will not have to wear an oral appliance, and will therefore not sacrifice taste, eating, or speech in order to achieve the goal of plantar sensation. The lumbar back is an ideal site for plantar sensory replacement and augmentation (but is not the exclusive potential site for an output display), as it has nearly identical two-point discrimination properties (static tactile, electrotactile and vibrotactile) in comparison to the plantar foot, and it comprises a location that would typically not be involved in peripheral neuropathy. Moreover, the device can be easily worn under clothing and is therefore discrete and socially acceptable. The device has a low-profile, ergonomic design, utilizing low power consumption. Although the present embodiment is described using the example of a device mounted to the back using a belt, other types of devices are also possible for use as output devices. In addition to the belt other methods of ensuring the back display is held in place are for example, gel type skin contacts, tight fitting clothing, or other materials that will allow for contact with the skin. For example, the stimulators may be worn in isolation (worn via an adhesive and/or bandage based, for example), socks, casts, anklets, air-casts, splints, prosthetics and dressings themselves, any article of clothing (gloves, shirts, undergarments, hats, belts, watches, necklaces), or a blanket or pad that may be placed on any anatomic location of interest. Advantages provided by incorporating the input device in other locations, such as hats or blankets include identification of areas in danger of pressure sore development in at-risk patients.

In one example, plantar sensors convey information to the lumbar back via the stimulator illustrated in FIG. 8. The sensor locations are determined by areas in the foot prone to over-pressure, and therefore, complications of peripheral neuropathy, for any reason. For example, the sensors in the display are the same as those shown in FIG. 3. In another example, the sensors are in the back display in analogous locations to the areas L1-L7 and R1-R7 described with reference to FIG. 7.

The vibrations or stimulus applied to the back are presented in a particular pattern, and will have a fluctuating frequency. Each pressure sensor in the insole will correspond to a stimulator over the back. The array applied to the back will be fashioned to represent the input (e.g. an insole-shaped area on the back would correspond to an insole-shaped area that is being measured). Frequency of the stimulus exerted by any particular stimulator will change according to the pressure measured by the corresponding sensor in the input device. For example, a higher pressure would correspond to a higher frequency stimulus. As the pressure input magnitude changes over time (e.g. over the course of the gait cycle), so too does the intensity of the corresponding stimulus felt on the back.

In addition to providing feedback via a real-time stimulus (e.g. electrotactile), the back display will also alert the user if a safety threshold has been exceeded. In the case of an electrotactile system, the voltage that stimulates the back will vary in accordance with the pressure encountered by the foot. If the pressure safety threshold has been exceeded, for example, the user can be alerted by way of a) an increase in the voltage; b) a beep; or c) a vibration at the location corresponding to where the thresholds has been exceeded. The vibrating function would function as the best alerting/localizing feature. This alert would only subside when pressure is offloaded, and force encountered is within a normal, safe range.

Further, in any display contacting the user's body (including the wristwatch or back display), a stimulator can amplify the body's feedback.

Further, the stimulator could either be overlapped with the sensor or immediately adjacent to it. In such a case, the stimulators would be located within the insole itself (or sock, etc.) as with the sensors. When the input device is a sock or a shoe, which gives greater coverage than the sole of the foot, the position of the stimulators can change.

Preferred modes of stimulation are electrotactile and vibrotactile. These are preferable for ergonomics in terms of creating a lower profile display. These would also be more comfortable to the user.

The back display can be realized in male and female styles, and in a spectrum of sizes dictated by waist circumference. For example, sizes can cover a waist circumference range between 23-50 inches. An exemplary back display is fitted to the patient for maximum comfort.

The output device employed herein may be a Tongue Display Unit (TDU).

V. System Power and Power Management

The power for the system in the exemplary case could employ a coin cell battery. Other power options include any other form of battery, a battery pack, an electrical cord designed to be plugged in to a power source, solar-powered, and/or self-powered (kinetic/movement, temperature, moisture, friction).

The system (communication, sensors, chipset) will have standard low-power features; the software programming will be optimized to further increase power savings.

VI. Further Modifications

Other possible sensor-based replacement, augmentation and analysis systems include systems that monitor any anatomic location of interest. For example, real-time solutions can be provided to monitor pressures on either prosthetic hands or gloves for hands deficient of sensation (e.g. those following certain Brachial Plexus injuries), and on the sacrum in quadriplegic and paraplegic patients. Sensors can be affixed with a glove, pads that attach to certain areas of the hand, or it can be built into prosthetics. These variations on the system may assist amputees, or patients that are prone to bedsores (e.g. bedridden, quadriplegic and paraplegic patients).

More specialized devices are also possible that offer highly technical users more sophisticated features, such as higher resolution systems and alternate anatomic sites and methods for relay of pressure or force data. In other examples, the input device can include sensors that monitor: GPS, heart rate, respiratory rate, blood pressure, temperature, blood oxygen saturation, blood flow, blood or environmental content quantification (e.g. glucose, electrolytes, minerals, oxygen, carbon dioxide, carbon monoxide, HbA1C, Ethanol, protein, lipid, carbohydrate, cortisol, lactate, pH, pro- and anti-inflammatory markers, MMPs, Growth Factors, bacterial content), hydration status/tissue turgor, joint position, features of gait analysis (including supination, pronation), device breakdown, pedometry, accelerometry, velocity, calorimetry, centre of gravity or centre of foot position, friction, traction, contact area, connectivity/insulation, EEG data, and/or ECG data. Sensors measuring blood flow may use an external laser. This technology allows prediction of ulceration weeks before there are clinical signs of disease.

As discussed above, pressure or force sensors can be spaced as shown in FIGS. 3-5. For electro-tactile (or other sensory) feedback, the comprehensive sensor grid illustrated in FIG. 5 is beneficial for providing a sufficient amount of data. However, moisture and temperature data, for example, will not have to be collected in grid-like format and so only a few sensors in strategic places will be needed. For example, some configurations may include only three to five sensors, with sensors located at the heel, toes and arch. A grid of sensors of one type can be overlain on another, provided that they do not contact the same point, i.e. a checkerboard pattern. For example, a blood flow sensor could be placed at the arch of the foot, where skin is the thinnest.

Regarding modifications for an athlete's foot manipulation, one way of quantitatively analyzing athletic (especially running) performance is by assessing body kinetics and kinematics in a lab setting (a "Human Performance Lab"). The benefit of this set-up is a highly structured environment, designed to facilitate the acquisition of quantitative data pertaining to all aspects of the gait cycle ("gait analysis"). The overarching disadvantage is the artificial (simulated) nature of this set-up, which inherently places limits on the generalizability of these results to the "real world."

The system has the advantage of using sensor-based data (especially pressure data) in an effort to quantify kinetics and kinematics in a "real world" situation. For example, one problem that may be identified in a Human Performance Lab is "over-supination" of the foot. The present device would be able to identify this situation—on a real-time, real-world basis by recognizing relatively higher pressures on the lateral side of the insole, and appropriately alerting the user. Failure to acknowledge abnormal wear patterns, such as this, could result in mechanical problems and sports injuries. In this way, athletic performance and endurance may be optimized.

In the case of athletics, the sensors of utmost importance are: pressure, acceleration/velocity/distance, and GPS.

As illustrated in examples shown in FIG. 2, sensor data is broadcast to many potential units, such as a dongle, a USB stick, the wristwatch discussed above, a TV, a personal computer or laptop, another other display (including an LCD display) and/or an electro-tactile (or other) back (or other body part) display. As discussed above, the electrotactile back display would use electrical impulses to stimulate the low back to transpose the pressures measured by the sensors in the insole. Electrical impulses in the electrotactile back display are strong enough to stimulate the nerve but not cause contraction in the muscle. Since the strength of the impulses needed vary between patients, the power can be made adjustable by way of scaled increments.

Although the illustrated example of the back display includes a belt holding the display in place so that electrodes do not shift, the electrodes could be held in place by an adhesive conducting gel that is in contact with the skin.

Obviously, numerous modifications and variations of the present disclosure are possible in light of the above teachings. It is therefore to be understood that within the scope of the appended claims, the invention may be practiced otherwise than as specifically described herein.

We claim:

1. A sensor-based quantification and analysis system, comprising:

an input device including
  a plurality of sensors, each sensor generating an input based on a force, and electronic transmission circuitry that transmits force information based on each of the generated inputs;
an output device that receives the force information; and
processing circuitry configured to select, for each sensor of the plurality of sensors, one of a plurality of levels of a likelihood of tissue damage based on a number of inputs generated by a respective sensor of the plurality of sensors within a predetermined time period indicating that a pressure threshold has been exceeded, and each of the plurality of levels of the likelihood of tissue damage is a threshold percentage of the inputs generated by the respective sensor within the predetermined time period indicating that the pressure threshold has been exceeded,
wherein the predetermined time period shifts with a passage of time for continuous monitoring, and wherein the output device includes a tactile display that presents the one of the plurality of levels of the likelihood of tissue damage for each sensor of the plurality of sensors.

2. The system according to claim 1, wherein the input device further includes a sensor that senses supersensory data, the transmission circuitry transmits supersensory information based on the supersensory data to the output device, and the output device presents feedback data based on the supersensory information.

3. The system according to claim 1, the tactile display being at least one of electro-tactile, vibro-tactile, and temperature-tactile, and wherein the tactile display is configured to be affixed to a back of a user.

4. The system according to claim 3, wherein the tactile display is arranged to provide a neuroplastic effect.

5. The system according to claim 1, wherein the output device logs and stores the one of the plurality of levels of the likelihood of tissue damage for at least one sensor of the plurality of sensors.

6. The system of claim 5, wherein the output device logs and stores the one of the plurality of levels of the likelihood of tissue damage remotely from the input device.

7. The system according to claim 1, wherein the output device presents the one of the plurality of levels of the likelihood of tissue damage for at least one sensor of the plurality of sensors using an auditory method.

8. The system according to claim 1, further comprising a visual display, the visual display being configured to display a plurality of areas corresponding to locations of the plurality of sensors.

9. The system according to claim 1, wherein the output device includes a wristband.

10. The system according to claim 1, wherein the input device further includes a temperature sensor and a moisture sensor, the transmission circuitry transmits information based on a temperature sensed by the temperature sensor and a moisture sensed by the moisture sensor, and the output device presents the information based on the temperature and the moisture.

11. The system according to claim 1, wherein the processing circuitry is located in at least one of the input device and the output device.

12. The system of claim 1, wherein the levels of the likelihood of tissue damage are based on a location of the generated inputs on a user's body.

13. The system of claim 12, wherein at least a portion of the plurality of sensors are located relative to one another to correspond to bony prominences of the user's foot.

14. The system of claim 13, wherein the portion of the plurality of sensors corresponding to the bony prominences of the user's foot are at a higher risk category than sensors corresponding to other areas of the user's foot.

15. The system of claim 14, wherein the higher risk category is defined by a lower pressure threshold.

16. The system of claim 14, wherein the higher risk category is defined by a lower threshold percentage of inputs indicating that the pressure threshold has been exceeded.

17. A sensor-based quantification and analysis system, comprising:
an input device including
  means for generating a plurality of inputs based on a force located to at least two regions on a user,
  electronic transmission circuitry that transmits force information based on the generated plurality of inputs;
an output device that receives the force information; and
means for selecting, at each region of the at least two regions of the user, one of a plurality of levels of a likelihood of tissue damage at a respective region of the at least two regions of the user based on the plurality of inputs generated at the respective region within a predetermined time period indicating that a pressure threshold has been exceeded, and each of the plurality of levels of the likelihood of tissue damage is a threshold percentage of the plurality of inputs generated at the region within the predetermined time period indicating that the pressure threshold has been exceeded,
wherein the predetermined time period shifts with a passage of time for continuous monitoring, and wherein the output device includes a tactile display that presents the one of the plurality of levels of the likelihood of tissue damage.

18. A quantification and analysis method, comprising:
generating by each sensor of a plurality of sensors, an input based on a force;
transmitting by a transmitter, force information based on each of the generated inputs; receiving the force information;
selecting by processing circuitry, for each sensor of the plurality of sensors, one of a plurality of levels of a likelihood of tissue damage based on a number of inputs generated by a respective sensor of the plurality of sensors within a predetermined time period indicating that a pressure threshold has been exceeded, each of the plurality of levels of the likelihood of tissue damage is a threshold percentage of the inputs generated by the respective sensor within the predetermined time period indicating that the pressure threshold has been exceeded; and
presenting a tactile feedback to a user, the tactile feedback corresponding to the one of the plurality of levels of the likelihood of tissue damage for each sensor of the plurality of sensors, wherein the predetermined time period shifts with a passage of time for continuous monitoring.

19. A sensor-based quantification and analysis system, comprising:
an input device including
means for generating a plurality of inputs based on a force located to at least two regions on a user, and electronic transmission circuitry that transmits force information based on the generated plurality of inputs; and an output device that receives the force information and includes means for selecting, at each region of the at least two regions of the user, one of a plurality of levels of a likelihood of tissue damage at a respective region of the at least two regions of the user based on a number of the plurality of inputs generated at the region within a predetermined time period indicating that a pressure threshold has been exceeded, and each of the plurality of levels of the likelihood of tissue damage is a threshold percentage of the plurality of inputs generated at the respective region within the predetermined time period indicating that the pressure threshold has been exceeded, wherein the predetermined time period shifts with a passage of time for continuous monitoring, and wherein the output device includes a tactile display that presents the one of the plurality of levels of the likelihood of tissue damage.

\* \* \* \* \*